United States Patent
Rakshit (10) Patent No.: US 10,832,118 B2
(45) Date of Patent: Nov. 10, 2020

(54) SYSTEM AND METHOD FOR COGNITIVE CUSTOMER INTERACTION

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

(*) Notice: Subject to any disclaimer, the term of this patent is extended or adjusted under 35 U.S.C. 154(b) by 360 days.

(21) Appl. No.: 15/903,199

(22) Filed: Feb. 23, 2018

(65) Prior Publication Data

US 2019/0266471 A1 Aug. 29, 2019

(51) Int. Cl.
| | | |
|---|---|---|
| G06Q 30/00 | (2012.01) | |
| G06N 3/00 | (2006.01) | |
| G06K 9/00 | (2006.01) | |
| G10L 15/18 | (2013.01) | |
| G06F 40/30 | (2020.01) | |

(52) U.S. Cl.
CPC ............ *G06N 3/008* (2013.01); *G06F 40/30* (2020.01); *G06K 9/00335* (2013.01); *G06Q 30/01* (2013.01); *G10L 15/18* (2013.01)

(58) Field of Classification Search
CPC .... G06N 3/008; G06F 40/30; G06K 9/00335; G06K 9/00677; G06Q 30/01; G06Q 30/0271; G06Q 30/0272; G10L 15/18; A61B 5/116; A61B 5/00; A61B 5/7275
USPC .......................................... 705/14.66, 14.67
See application file for complete search history.

(56) References Cited

U.S. PATENT DOCUMENTS

| | | | | |
|---|---|---|---|---|
| 6,651,044 | B1 * | 11/2003 | Stoneman | G06N 20/00 706/10 |
| 8,983,889 | B1 * | 3/2015 | Stoneman | G06Q 99/00 706/46 |
| 9,083,801 | B2 | 7/2015 | Conway et al. | |
| 9,375,845 | B1 * | 6/2016 | Annan | B25J 11/0005 |
| 9,724,824 | B1 * | 8/2017 | Annan | B25J 11/0005 |
| 2007/0142965 | A1 * | 6/2007 | Lin | G06N 3/008 700/245 |

(Continued)

OTHER PUBLICATIONS

This humanoid robot can recognize and interact with people; Business Insider India, Reuters, Apr. 20, 2015, https://www.businessinsider.in/This-humanoid-robot-can-recognize-and-interact-with-people/articleshow/46993046.cms, printed Feb. 22, 2018; 7 pages.

Dautenhahn, Kerstin; Human-Robot Interaction; The Encyclopedia of Human-Computer Interaction, 2nd Ed.; https://www.interaction-design.org/literature/book/the-encyclopedia-of-human-computer-interaction-2nd-ed/human-robot-interaction; printed Feb. 22, 2018; 85 pages.

(Continued)

*Primary Examiner* — Luis A Brown
(74) *Attorney, Agent, or Firm* — Christopher M. Pignato (57) ABSTRACT

The present invention is a system and method for cognitive customer interaction. The system includes a humanoid robot having a processor operably connected to a camera and a speaker within the robot. The system has a social interactions database connected to the processor. The social interactions database stores interaction patterns representing speech, facial expressions, and body movement. An advanced analytics program, such as Watson Analytics, determines the identity of a customer in a store and performs social content analysis of the customer on social media platforms. The advanced analytics program generates a psycholinguistic profile of the user so gestures and speech of the customer is compared to the psycholinguistic profile and the humanoid robot may response appropriately.

18 Claims, 5 Drawing Sheets

(56) References Cited

U.S. PATENT DOCUMENTS

| | | | | |
|---|---|---|---|---|
| 2007/0192910 | A1* | 8/2007 | Vu | G05D 1/0274 700/245 |
| 2012/0284080 | A1* | 11/2012 | De Oliveira | G06Q 30/0202 705/7.29 |
| 2012/0316676 | A1* | 12/2012 | Fouillade | B25J 9/1697 700/246 |
| 2013/0218339 | A1* | 8/2013 | Maisonnier | B25J 13/003 700/257 |
| 2014/0244359 | A1* | 8/2014 | Haber | G06Q 30/0204 705/7.33 |
| 2014/0270139 | A1* | 9/2014 | Conway | H04M 3/42161 379/265.06 |
| 2016/0199977 | A1* | 7/2016 | Breazeal | B25J 9/1694 700/246 |
| 2016/0275092 | A1* | 9/2016 | Black | G06F 3/0484 |
| 2016/0283465 | A1* | 9/2016 | Patris | G06N 3/008 |
| 2017/0113353 | A1* | 4/2017 | Monceaux | G10L 15/26 |
| 2017/0329872 | A1* | 11/2017 | Dispensa | G06F 7/24 |
| 2018/0090145 | A1* | 3/2018 | Kume | G10L 15/22 |
| 2018/0229372 | A1* | 8/2018 | Breazeal | B25J 11/001 |
| 2019/0143527 | A1* | 5/2019 | Favis | B25J 13/003 700/264 |
| 2019/0245812 | A1* | 8/2019 | Rico | A63F 13/73 |
| 2019/0266471 | A1* | 8/2019 | Rakshit | G06F 40/30 |

OTHER PUBLICATIONS

Wikipedia; Human-Robot Interaction; https://en.wikipedia.org/wiki/Human%E2%80%93robot_interaction; printed Feb. 22, 2018; 5 pages.

Feil-Seifer, David and Maja J. Mataric; Human-Robot Interaction; http://robotics.usc.edu/publications/media/uploads/pubs/585.pdf; printed Feb. 22, 2018; 20 pages.

Nourbakhsh, Illah R., et al; 16867 and 16899D: Principles of Human-Robot Interaction; Robotics Institute Carnegie Mellon University; 2015; http://www.cs.cmu.edu/~illah/ri899.html; printed Feb. 22, 2018; 3 pages.

Human=centered Assistive Robotics; Associate Professorship of Human-centered Assistive Robotics; TUM Department of Electrical and Computer Engineering; Technical University of Munich; http://www.hcr.ei.tum.de/en/home/; printed Feb. 22, 2018; 3 pages.

Takahashi, Dean; IBM researcher can decipher your personality from looking at 200 of your tweets; Oct. 8, 2013; https://venturebeat.com/2013/10/08/ibm-researcher-can-decipher-your-personality-in-200-tweets/; printed Feb. 22, 2018; 6 pages.

Takahashi, Dean; How IBM's Michelle Zhou figured out my personality from 200 tweets (interview); Oct. 11, 2013; https://venturebeat.com/2013/10/11/how-ibms-michelle-zhou-figured-out-my-personality-from-200-tweets-interview/; printed Feb. 22, 2018; 5 pages.

* cited by examiner

SYSTEM AND METHOD FOR COGNITIVE CUSTOMER INTERACTION

BACKGROUND

The present invention relates generally to cognitive customer interaction, humanoid robots, social media and networking content analyses.

A customer typically enters a store or showroom looking to purchase a product or learn more about products offered for sale. Retail salespersons or other showroom staff is typically trained to approach the customer to provide product information, answer the customer's questions, and persuade the customer to purchase the products. As such, salespersons need refined customer interaction skills. Many times, salespersons and other retails employees are not able to effectively communicate with customers. As a result of ineffective communication, customers may delay making a purchasing decision, become dissatisfied with the shopping experience, buy from a competing business, etc.

As a result, human robot interaction (HRI) has been studied and adapted as a potential solution to address the problem of customer satisfaction in hospitality and retail industries. Humanoid robots have been developed with human-like skin, cameras and sensors in their bodies, such as in the eyes, and speakers in their mouths. A typical humanoid robot speaks via the speaker and makes facial expression using motors in its face. Thus, it is possible for the humanoid robots to interact with humans in meaningful ways, such as for customer service purposes.

Psycholinguistics is the study of the psychological and neurobiological factors involved in human acquisition, use, comprehension and production of natural language. The discipline is largely concerned with the mechanisms used to process and represent natural language in the brain. Modern psycholinguistic research makes use of biology, neuroscience, cognitive science, linguistics, and information science to study how the brain processes language. There are a number of subdisciplines with non-invasive techniques for studying the neurological workings of the brain; for example, neurolinguistics has become a field in its own right. Psycholinguistics has roots in education and philosophy. Psycholinguistics covers the cognitive processes that make it possible to generate a grammatical and meaningful sentence out of vocabulary and grammatical structures. Psycholinguistics further covers processes that make it possible to understand utterances, words, text, etc.

SUMMARY

The present invention is a system and method for cognitive customer interaction. In one embodiment, the invention is a method for cognitive customer interaction. The method includes the steps of: (i) receiving, by an analytics program, social media data set including information indicative of a user's natural language based interactions with a plurality of associates of the user; (ii) determining, by the analytics program, an aggregated psycholinguistic profile of the associates of the user; (iii) generating, by the analytics program, a first natural language text based in part upon the aggregated psycholinguistic profile; and (iv) communicating, through a user interface, the first natural language text to the user.

In an embodiment of the method, the user interface includes a humanoid robot.

In another embodiment of the method, the first natural language text includes information about a product or service that the user is potentially interested in purchasing.

In yet another embodiment of the method, the psycholinguistic profile includes values for at least the following categories: social behavior, values, needs and personality.

In another embodiment of the method, the personality category includes sub-values for at last the following sub-categories: agreeableness, conscientiousness, openness, extraversion and neuroticism.

In an embodiment of the method, the plurality of associates of the first user are friends of the first user; and the determination of the an aggregated psycholinguistic profile includes for each given friend of the plurality of associates: analysis of natural language communications directed by the given friend to the user, and determining insight into psycholinguistic dimensions of the user based, at least in part, upon the analysis of natural language communications directed by the given friend to the user.

In another embodiment, the invention is a computer program product. The computer program product includes a computer readable storage medium and a computer code stored on the computer readable storage medium, with the computer code including instructions and data for causing a processor(s) set to perform at least the following operations: (i) receiving, by an analytics program, social media data set including information indicative of a user's natural language based interactions with a plurality of associates of the user, (ii) determining, by the analytics program, an aggregated psycholinguistic profile of the associates of the user, (iii) generating, by the analytics program, a first natural language text based in part upon the aggregated psycholinguistic profile, and (iv) communicating, through a user interface, the first natural language text to the user.

In an alternative embodiment, the invention is a computer system. The method includes a processor(s) set, a computer readable storage medium and a computer code stored on the computer readable storage medium, with the computer code including instructions and data for causing the processor(s) set to perform at least the following operations: (i) receiving, by an analytics program, social media data set including information indicative of a user's natural language based interactions with a plurality of associates of the user, (ii) determining, by the analytics program, an aggregated psycholinguistic profile of the associates of the user, (iii) generating, by the analytics program, a first natural language text based in part upon the aggregated psycholinguistic profile, and (iv) communicating, through a user interface, the first natural language text to the user.

BRIEF DESCRIPTION OF THE DRAWINGS

The present invention will be more fully understood and appreciated by reading the following Detailed Description in conjunction with the accompanying drawings, in which.

DETAILED DESCRIPTION

Referring to the Figures, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
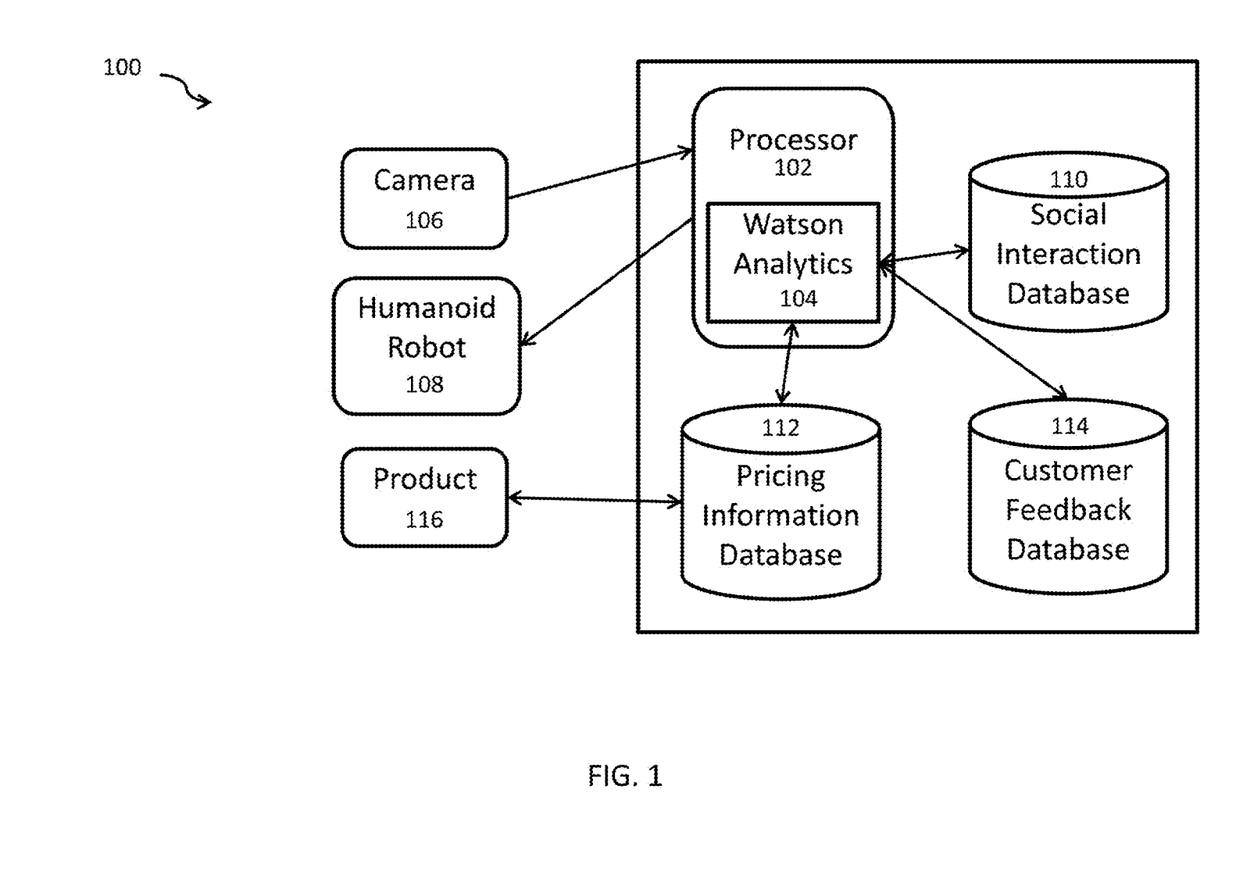
FIG. 1 is a diagram of a non-limiting illustrative embodiment of the system for cognitive customer interaction.

Some embodiments of the present invention may recognize one, or more, of the following facts, problems, drawbacks, challenges or areas for potential improvement with respect to the current state of the relevant art: (i) although humanoid robots can execute verbal and body movement tasks, humanoid robots lack the ability to perceive social cues; (ii) there is a need for a system and method for cognitive interaction; (iii) there is a need for a humanoid robot that uses cognitive interaction to communicate with customers in the hospitality and retail industries in meaningful ways; and/or (iv) there is a need for a humanoid robot that uses cognitive interaction to communicate with customers in the hospitality and retail industries in ways that increase customer satisfaction. Referring again to the drawings, wherein like reference numerals refer to like parts throughout, there is shown in FIG. 1 a diagram of a non-limiting illustrative embodiment of the system 100. The system 100 comprises a processor 102 configured to perform advanced analytics. In the depicted embodiment, the system 100 utilizes Watson Analytics 104, which is performed by the processor 102. Watson Analytics 104 provides predictive analyses and cognitive analyses for large amounts of data. Watson Analytics 104 also analyzes social media data for processing at the processor 102. Although the system 100 shown in FIG. 1 utilizes Watson Analytics 104, other advanced analytics programs can be utilized.

Still referring to FIG. 1, the system 100 comprises a camera 106 connected to the processor 102. The connection between the camera 106 and the processor 102 may be wired or wireless. In one embodiment, a store, shop, other retail space has one or more cameras 106 placed on the walls (or other surfaces). In another embodiment, the camera 106 is located on a humanoid robot 108 within the store, shop, or other retail space. Alternative placement of the camera 106 is contemplated where the camera has customers (or other persons) within its field-of-view.

In the embodiment, wherein the humanoid robot 108 comprises one or more cameras 106, the humanoid robot 108 is configured to interact with customers in a store or showroom. In such an embodiment, the humanoid robot 108 may comprise all or most of the elements of the system 100. For example, the processor 102 and databases 110, 112, 114 may be stored within the humanoid robot 108 and connected via known hardware, such as printed circuit boards (PCBs). The humanoid robot 108, generally, as known in the art, can speak via internal speakers and mimic human expressions via internal motors.

Also shown in FIG. 1, the system 100 also comprises a social interaction database 110. The social interaction database 110 stores data representing body language, facial patterns, speech patterns, tone of voice, and other social cues. The social cues are associated with attitudes, feelings, and thoughts. For example, body language such as crossed or folded arms and speech patterns which are short and concise may be associated with attitudes and feelings of anger, dislike, or disappointment. The social interaction database 110 transmits data to the processor 102 for analyses (by Watson Analytics 104) and receives data that is learned from such analyses.

In alternative embodiments, the system 100 also comprises a pricing information database 112, a customer feedback database 114, and one or more products 116 from the store. The pricing information database 112 stores data regarding the price of each product 116 in the store, the price of the same or similar products 116 offered at competing stores, and the numbers of products 116 sold, for example. The customer feedback database 114 stores data extracted from customer reviews. For example, the customer feedback database 114 may store data regarding a customer's experience interacting with the humanoid robot 108 at the store or the customer's experience using the product 116 purchased.

Figure 2:
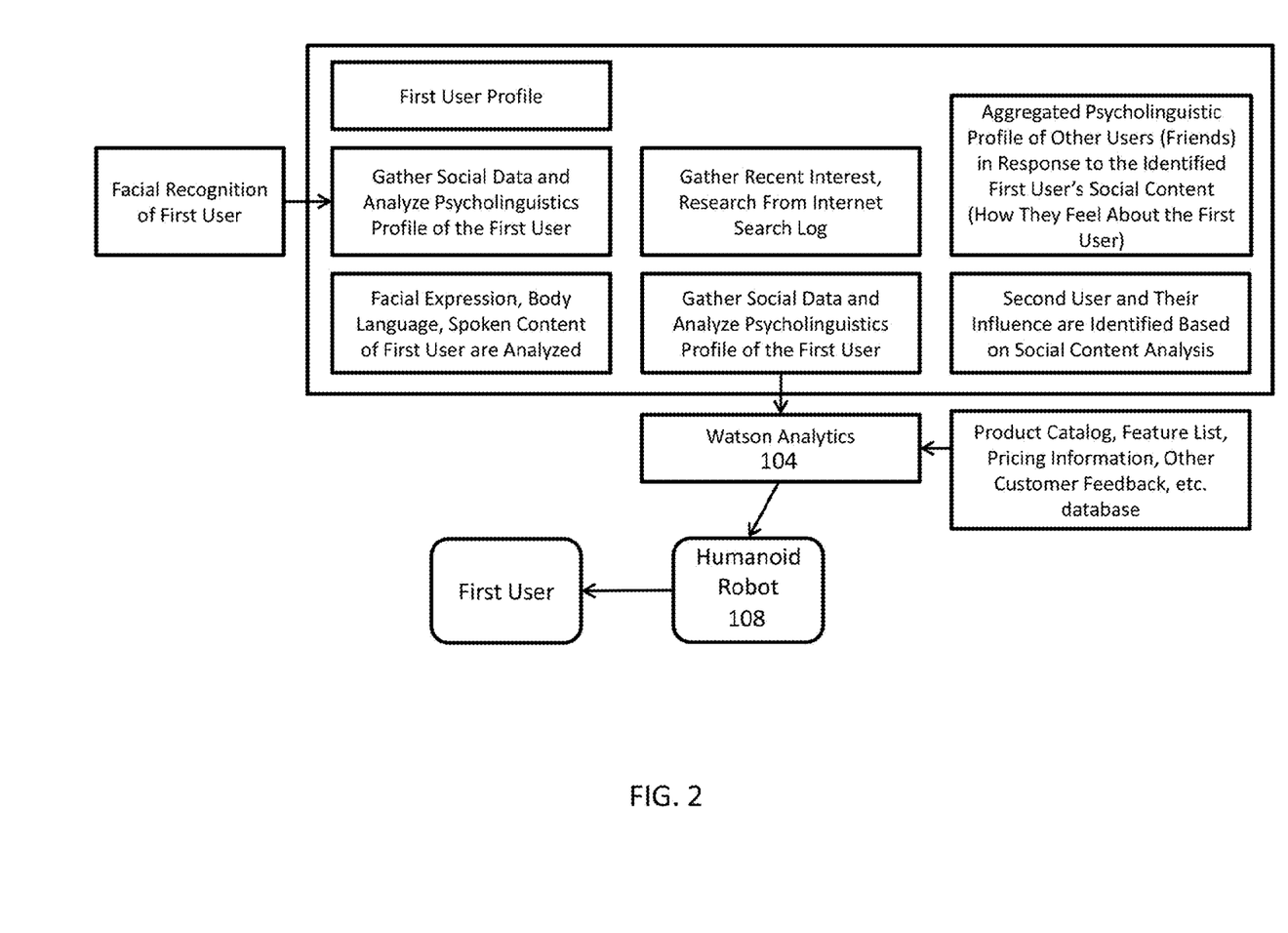
FIG. 2 is a diagram of a non-limiting illustrative embodiment of a method for cognitive customer interaction.

Referring now to FIG. 2, there is a diagram of a non-limiting illustrative embodiment of a method for cognitive customer interaction. The method for cognitive customer interaction is initiated upon entry of one or more users into an environment, such as a shop, store, or other retail space equipped with the system 100. At the first step, the system 100 recognizes the face of a first user via facial recognition programming. The camera 106 (or any other similar capturing mechanism) of the system 100 identifies the first user. The system 100 receives the image of the first user from the camera 106 and performs facial recognition by searching one or more social networking sites for photographs or other instances of the first user's face. Such searching and analyses of social networking sites is performed by Watson Analytics 104 (or some other similar advanced analytics program).

At the second step, the system 100 detects a second user, accompanying the first user. Again, the camera 106 identifies the second user through facial recognition by capturing an image and facial features of the second user and searching one or more social networking sites for instances of the second user's face. Thus, the camera 106 identifies the first user and the second user individually.

At the third step, after identifying the second user, the system 100 identifies a relationship between the first user and the second user. Upon identifying the relationship, the system 100 determines the strength of the relationship using social content analysis performed by Watson Analytics 104 (or another advanced analytics program). For example, in one embodiment, if the relationship between the first user and the second user is familial, the strength of the relationship may be determined to be strong. In another example, the social content analysis (via Watson Analytics 104) may determine the relationship is weak if the first user and the second user are acquaintances or new friends.

At the next step, the system 100, utilizing social content analysis (again, via Watson Analytics 104), determines and identifies which of the first user and the second user is most likely to be a customer. Of the first and second users, the identified customer is the one most likely to make a purchase in the store, shop, or retail space. In the embodiments described herein, the first user is the identified customer, although it is contemplated the second user, both users, and neither users may be identified customers.

Figure 5:
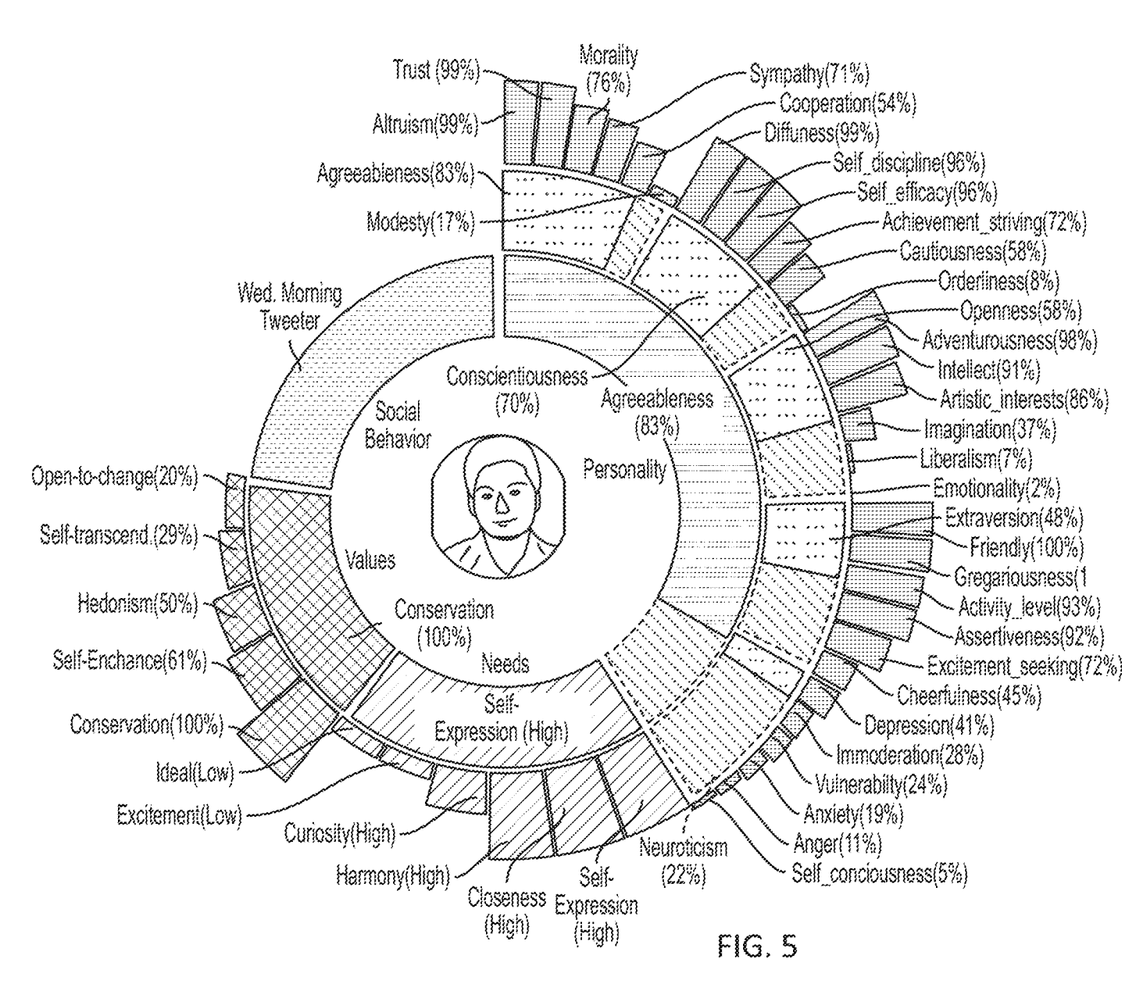
FIG. 5 is a diagram of a non-limiting illustrative embodiment of a psycholinguistic profile.

At the next step, the system 100 will extract social content individually for both the first user and the second user. Such social content includes any data from social network and social media platforms. Examples of social network and social media platforms include Twitter, Facebook, and the like. At the following step, based on the social content extracted, the system 100 performs and creates a psycholinguistic profile for each identified customer, individually. In the depicted embodiment, a psycholinguistic profile is created for the first user. A diagram of a non-limiting illustrative embodiment of a psycholinguistic profile is shown in FIG. 5.

After the psycholinguistic profile is created for the first user, the identified customer, the system 100 searches and collects data regarding friends of the first user. The term "friends" is used to describe any relationships with others on social media, such as followers and connections, for example. The system 100 (again, via Watson Analytics 104) gathers data pertaining to any interactions between the friends and the first user. The total interaction for each individual friend and the first user is quantified and compared to a threshold limit. If the total interaction found is above a threshold limit of interaction, the system 100 will identify a psycholinguistic profile for that friend. As it is possible (and likely) that the first user will have interactions with numerous friends that exceeds the threshold limit, the system 100 can identify numerous psycholinguistic profiles, one per each friend.

Figure 3:
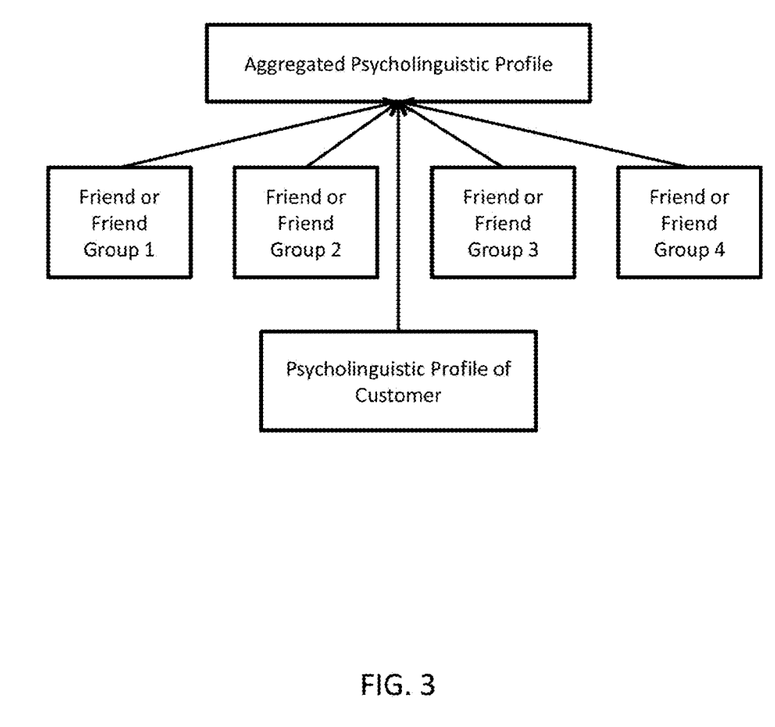
FIG. 3 is a diagram of a non-limiting illustrative embodiment of psycholinguistic profile aggregation.

Referring briefly to FIG. 3, there is shown a diagram of a non-limiting illustrative embodiment of psycholinguistic profile aggregation. At the following step, the interactions which exceed the threshold limit are analyzed by the system 100 (i.e., Watson Analytics 104). The system 100 analyzes the contents of the interactions for each friend, determining how the friend responds to the first user. Accordingly, the system 100 then creates an aggregated psycholinguistic profile of the friends, as shown in FIG. 3. The aggregated psycholinguistic profile provides insight on how the friends feel and think about the first user. Thus, the aggregated psycholinguistic profile is created based on social content from the first user's social media and social networking platforms and interactions with friends when the interactions exceed a threshold amount or significance. The purpose of the aggregated psycholinguistic profile is to create a better or more accurate overall psycholinguistic profile for the first user based on a broader scope of data and social content.

Figure 4:
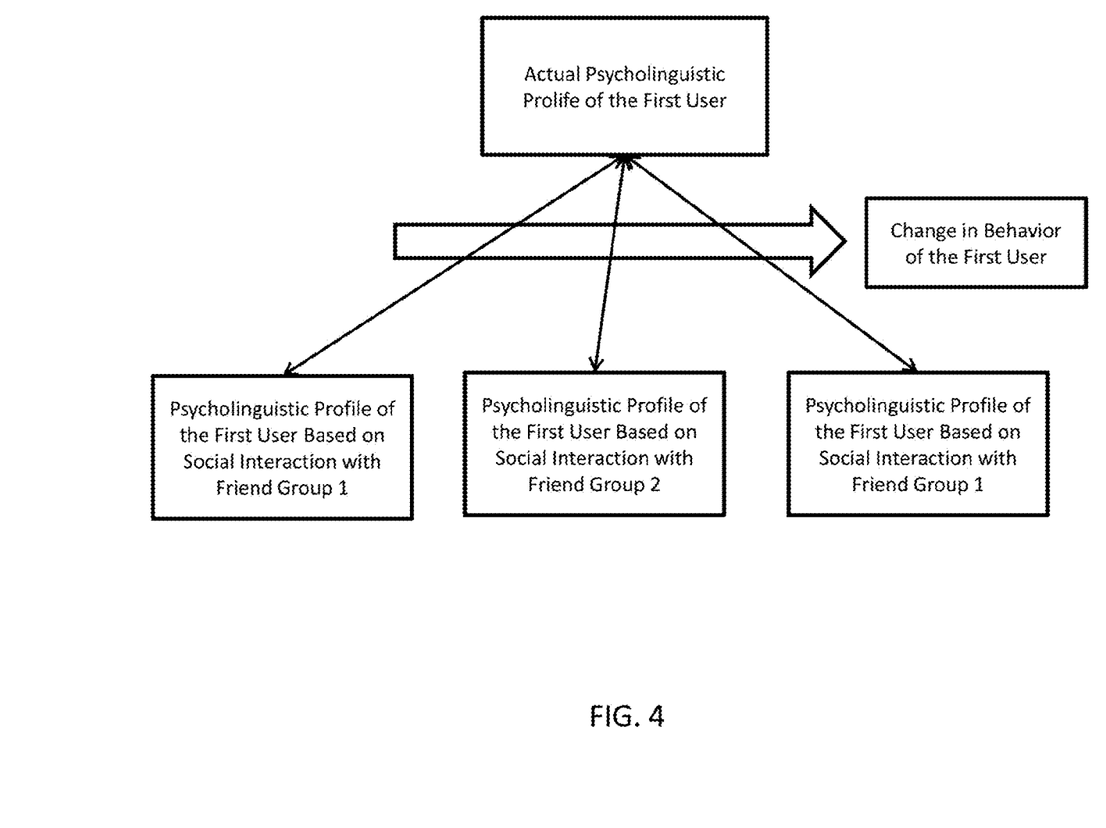
FIG. 4 is a diagram of a non-limiting illustrative embodiment of behavioral analysis.

Referring now to FIG. 4, there is shown a diagram of a non-limiting illustrative embodiment of behavioral analysis. In one embodiment, the system 100 compares the interaction contents between a new friend (for the purposes of this disclosure "new friend" may mean a friend that has not yet been considered by the system 100 or a friend that has recently started interacting with the first user) and the first user to the first user's normal psycholinguistic profile. Through the comparison, the system 100 detects changes in the behavior during the interaction. The system 100 (via the processor 102) then selects the most suitable interaction pattern from the social interaction database 110 based on the changes in behavior. An example of an interaction pattern is: "customer does not feel offended, customer feels confident." After the suitable interaction pattern is selected, the humanoid robot 108 will interact according to the suitable interaction pattern with the first user, as shown in FIG. 2.

In another embodiment, the system 100 continuously analyzes movements of the first user. Such movements include body language and facial patterns, for example. Using the camera 106 and/or other applicable sensors, the system 100 can detect changes in movement of the first user. The system 100 then compares the change in movement to data pertaining to movement stored in the social interaction database 110. When a change in movement is matched or otherwise found significantly similar to a movement found in the social interaction database 110, a rule associated with the stored movement is then applied by the system 100 (via the processor 102). Based on the rule, the humanoid robot 108 performs a rule-based reaction.

In an additional embodiment, the system 100, again, via the camera 106 and/or other sensors, detects social interaction between the first user and the second user. When social interaction is detected between the first user and the second user, the system 100 (via Watson Analytics 104) analyzes the communication between the first user and the second user and identifies the effect the communication has on both the first user and the second user. In other words, the system 100 determines how the communication or interaction between the first user and the second user influences both parties.

Thus, the system 100 can understand the first user's behavior, likes, dislikes, influencing factors, and accordingly, identify appropriate questions and answers for the first user. As a result, the humanoid robot 108 can relay these questions and answers to the first user to increase the likelihood that the response is agreeable to the first user. As the first user is more likely to be satisfied with the conversation with the humanoid robot 108, the first user is more likely to make a purchase at that store, shop, or other retail space. In another embodiment, the humanoid robot 108 can be replaced with any other robot-like configuration that is not human-like.

In an alternative embodiment, the system 100 is connected to other apparatuses and systems in the store. For example, as shown in FIG. 1, the system 100 may be connected to products 116 in the store. Thus, the system 100 can analyze the psycholinguistic profiles of purchasers of a specific product 116 and identify similar customers. The system 100 may also connect to a pricing information database 112 and a customer feedback database 114. The pricing information database 112 contains data regarding the price of the same or similar products 116 at other shops, stores, and retail spaces. The customer feedback database 114 contains data regarding customer reviews of the experience interacting with the humanoid robot 108 or customer reviews of specific products. Data from the customer feedback database 114 is used to make adjustments in the store, shop, other retail space, including in the questions and answers provided by the humanoid robot 108, in the product 116 offerings, or in the price of the products 116, for example.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method for implementing cognitive interaction to communicate between a humanoid robot and a user comprising:
    configuring the humanoid robot with a processor configured to perform advanced analytics using an analytics program, a camera connected to the processor, a social interaction database, and internal speakers and motors configured to mimic human expressions;
    capturing, by the camera of the humanoid robot, an image of the user;
    identifying, by the analytics program of the humanoid robot, the user, using facial recognition by searching one or more social networking sites for photographs or other instances of the user's face;
    extracting, by the analytics program of the humanoid robot, a social media data set including information indicative of the user's natural language based interactions with a plurality of associates of the user;
    determining, by the analytics program, an aggregated psycholinguistic profile of the user and the plurality of associates of the user;
    generating, by the analytics program, a first natural language text based in part upon the aggregated psycholinguistic profile;
    communicating, through the internal speakers, the first natural language text to the user; and
    continuously analyzing, by the camera of the humanoid robot, movements of the user, including body language and facial pattern, detecting changes in movement of the user and comparing the changes in movement of the user to movement data stored by the social interaction database wherein when a change in movement is matched to movements of the social interaction database, the humanoid robot implements a rule based reaction provided by the social interaction database.

2. The method of claim 1 further comprising:
configuring the humanoid robot with a pricing information database containing product prices and a customer feedback database comprising customer reviews and experiences interacting with the humanoid robot; and
applying, by the humanoid robot, adjustments to a store, shop or retail space, including questions and answers provided from the humanoid robot to the user about product offerings and the product prices based on customer feedback stored by the customer feedback database.

3. The method of claim 1 wherein the first natural language text includes information about a product or service that the user is potentially interested in purchasing.

4. The method of claim 1 wherein the psycholinguistic profile includes values for at least the following categories: social behavior, values, needs and personality.

5. The method of claim 4 wherein the personality category includes sub-values for at last the following sub-categories: agreeableness, conscientiousness, openness, extraversion and neuroticism.

6. The method of claim 1 wherein:
the plurality of associates of the user are friends of the user; and
the determination of the aggregated psycholinguistic profile includes for each given friend of the plurality of associates:
analysis of natural language communications directed by the given friend to the user, and
determining insight into psycholinguistic dimensions of the user based, at least in part, upon the analysis of natural language communications directed by the given friend to the user.

7. A computer program product (CPP) for implementing cognitive interaction to communicate between a humanoid robot and a user comprising:
a computer readable storage medium; and
computer code stored on the computer readable storage medium, with the computer code including instructions and data for causing a processor set to perform at least the following operations:
configuring the humanoid robot with the processor set to perform advanced analytics using an analytics program, a camera connected to the processor, a social interaction database, and internal speakers and motors configured to mimic human expressions;
capturing, by the camera of the humanoid robot, an image of the user;
identifying, by the analytics program of the humanoid robot, the user, using facial recognition by searching one or more social networking sites for photographs or other instances of the user's face;
extracting, by the analytics program of the humanoid robot, a social media data set including information indicative of the user's natural language based interactions with a plurality of associates of the user,
determining, by the analytics program, an aggregated psycholinguistic profile of the user and the plurality of associates of the user,
generating, by the analytics program, a first natural language text based in part upon the aggregated psycholinguistic profile,
communicating, through the internal speakers, the first natural language text to the user; and
continuously analyzing, by the camera of the humanoid robot, movements of the user, including body language and facial pattern, detecting changes in movement of the user and comparing the changes in movement of the user to movement data stored by the social interaction database wherein when a change in movement is matched to movements of the social interaction database, the humanoid robot implements a rule based reaction provided by the social interaction database.

8. The CPP of claim 7 further comprising:
configuring the humanoid robot with a pricing information database containing product prices and a customer feedback database comprising customer reviews and experiences interacting with the humanoid robot;
applying, by the humanoid robot, adjustments to a store, shop or retail space, including questions and answers provided from the humanoid robot to the user about product offerings and the product prices based on customer feedback stored by the customer feedback database.

9. The CPP of claim 7 wherein the first natural language text includes information about a product or service that the user is potentially interested in purchasing.

10. The CPP of claim 7 wherein the psycholinguistic profile includes values for at least the following categories: social behavior, values, needs and personality.

11. The CPP of claim 10 wherein the personality category includes sub-values for at last the following sub-categories: agreeableness, conscientiousness, openness, extraversion and neuroticism.

12. The CPP of claim 7 wherein:
the plurality of associates of the user are friends of the user; and
the determination of the aggregated psycholinguistic profile includes for each given friend of the plurality of associates:
analysis of natural language communications directed by the given friend to the user, and
determining insight into psycholinguistic dimensions of the user based, at least in part, upon the analysis of natural language communications directed by the given friend to the user.

13. A computer system (CS) of a humanoid robot comprising:
a processor set configured to perform advanced analytics using an analytics program;
a camera connected to the processor set;
internal speakers and motors connected to the processor set, configured to mimic human expressions;
a computer readable storage medium; and
computer code stored on the computer readable storage medium, with the computer code including instructions and data for causing the humanoid robot to perform at least the following operations:
capturing, by the camera of the humanoid robot, an image of the user;
identifying, by the analytics program of the humanoid robot, the user, using facial recognition by searching one or more social networking sites for photographs or other instances of the user's face;
extracting, by the analytics program of the humanoid robot, a social media data set including information indicative of the user's natural language based interactions with a plurality of associates of the user, creating, by the analytics program, an aggregated psycholinguistic profile of user and the plurality of the associates of the user, generating, by the analytics program, a first natural language text based in part upon the aggregated psycholinguistic profile, communicating, through the internal speakers, the first natural language text to the user, and;

continuously analyzing, by the camera of the humanoid robot, movements of the user, including body language and facial pattern, detecting changes in movement of the user and comparing the changes in movement of the user to movement data stored by a social interaction database of the humanoid robot, wherein when a change in movement is matched to movements of the social interaction database, the humanoid robot implements a rule based reaction provided by the social interaction database.

14. The CS of claim 13 further comprising:

configuring the humanoid robot with a pricing information database containing product prices and a customer feedback database comprising customer reviews and experiences interacting with the humanoid robot; and applying, by the humanoid robot, adjustments to a store, shop or retail space, including questions and answers provided from the humanoid robot to the user about product offerings and the product prices based on customer feedback stored by the customer feedback database.

15. The CS of claim 13 wherein the first natural language text includes information about a product or service that the user is potentially interested in purchasing.

16. The CS of claim 13 wherein the psycholinguistic profile includes values for at least the following categories: social behavior, values, needs and personality.

17. The CS of claim 16 wherein the personality category includes sub-values for at last the following sub-categories: agreeableness, conscientiousness, openness, extraversion and neuroticism.

18. The CS of claim 13 wherein:

the plurality of associates of first user are friends of first user; and creating the aggregated psycholinguistic profile includes for each given friend of the plurality of associates:

analysis of natural language communications directed by the given friend to the user, and determining insight into psycholinguistic dimensions of the user based, at least in part, upon the analysis of natural language communications directed by the given friend to the user.

* * * * *